June 15, 1965 H. C. SWIM ETAL Plant Pat. 2,538
ROSE PLANT
Filed March 13, 1964
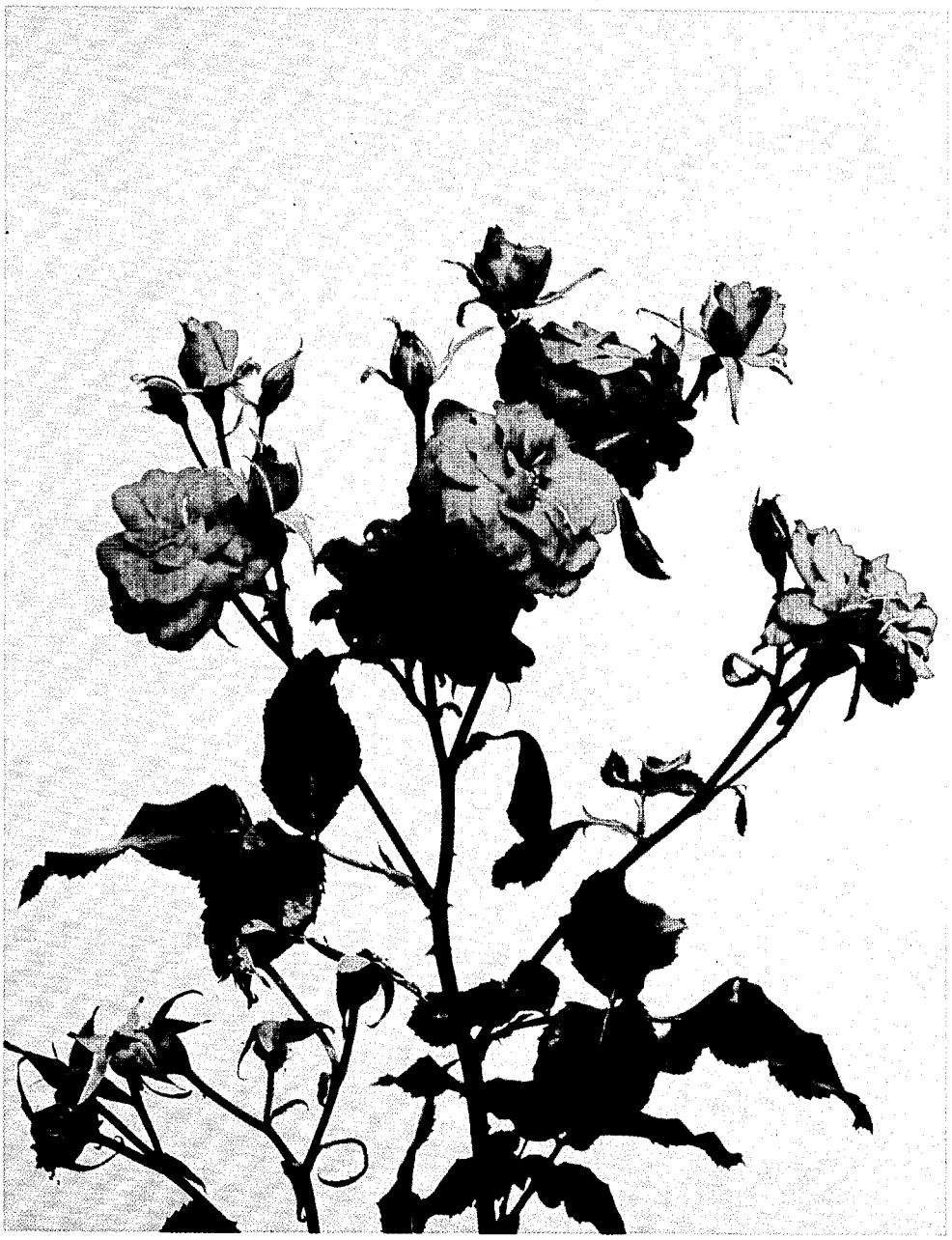
Inventors.
H. C. Swim and
O. L. Weeks
By: Robb & Robb
Attorneys.

United States Patent Office

Plant Pat. 2,538
Patented June 15, 1965

2,538
ROSE PLANT

Herbert C. Swim, Ontario, and O. L. Weeks, Chino, Calif., assignors to said O. L. Weeks, doing business as Weeks Wholesale Rose Grower, Chino, Calif.

Filed Mar. 13, 1964, Ser. No. 351,878
1 Claim. (Cl. Plt.—28)

The present invention relates to a new and distinct variety of rose plant of the floribunda class, which was originated by us by crossing the variety "Spartan" (Plant Patent No. 1,357) with the variety "Garnette" (unpatented).

As the result of this breeding, we have produced a new rose variety having the following unique combination of characteristics which are outstanding therein and which distinguish it from its parents, as well as from all other varieties of which we are aware:

(1) A relatively low growing and compact habit of growth;

(2) The production of flower buds of long-pointed to urn-shaped form;

(3) A flower size ranging from small to medium, with semi-double petalage;

(4) A habit of bearing the flowers in clusters composed of a relatively large number of flowers per cluster as compared with other varieties in this class having red colored flowers;

(5) Profuse production of flowers, with a consequent mass effect which substantially covers the plant;

(6) A distinctive and attractive Bright Red general color tonality of the flowers;

(7) Long-lasting flower qualities; and (8) Relative freedom from disease, and more particularly from powdery mildew.

In comparison with its seed parent "Spartan," the plant of our new variety is substantially lower growing; it bears many more flowers, with the flowers tending to substantially cover the plant at the peak of the bloom periods; the flowers are borne in clusters or sprays composed of a greater number of flowers on the average; the flowers are somewhat smaller in size, ranging from about 2¼ inches to 2¾ inches in diameter, as compared with 3 inches to 3½ inches in the case of the flowers of "Spartan"; the flowers of our new variety have less petalage, ranging from 25 to 30 petals, as compared with 30 or more petals in the case of the flowers of "Spartan"; and the flower color of our new variety is darker, ranging from Medium Red to Dark Red, as distinguished from the Orange-Red to Reddish-Coral flower color of "Spartan."

As compared with the pollen parent "Garnette" our new variety has a lower growing habit; the flower stems are substantially longer, with little evidence of the zigzag effect that is characteristic of the flower stems of "Garnette"; the flower buds have a form ranging from long-pointed to urn-shaped, as compared with the short-pointed to nearly globular flower buds of "Garnette"; the flowers have a substantially greater diameter but substantially fewer petals than those of "Garnette" in which the petalage averages about 50 petals per flower; and the flowers have a Bright Red color which is undiluted or altered with other colors, thus giving a distinctive and attractive mass effect without the characteristic Blue or Magenta shadings in the reddish flower color of "Garnette."

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Bush; outdoor; seedling; for garden decoration.
Class: Floribunda.
Breeding: Seedling.
*Seed parent.*—"Spartan."
*Pollen parent.*—"Garnette."
Propagation: Holds its distinguishing characteristics through succeeding propagations by budding.

*Flower*

Locality where grown and observed: Chino, California.
Flowers borne: From 3 to several to a stem; in irregular, flat to rounded clusters; on stems ranging from short to medium length and of normal strength.
Quantity of bloom: Abundant, outdoors.
Continuity: More or less continuous.
Fragrance: From slight to none.
Bud:
*Peduncle.*—Short; medium caliper; erect; medium rough; very many short stipitate glands. Color—reddish-green.
*Before calyx breaks.*—Size—small. Form—short; with a conspicuous neck (pericarp); with foliaceous appendages on the surface of the bud; nearly minimal foliaceous parts extending beyond the tip of the bud.
*As calyx breaks.*—Color—near Dark Red, Plate 2.5R 3/7.
*As first petal opens.*—Size—from small to medium. Form—from long-pointed to urn-shaped. Color: outside—near Moderate Red, Plate 2.5R 4/10; inside—near Strong Red, Plate 5R 4/12, with some overlay of Dark Red, Plate 2.5R 3/7.
*Opening.*—Opens up well.
Bloom:
*Size (when fully open).*—From small to medium; from 2¼ inches to 2¾ inches.
*Petalage.*—Semi-double; from 25 to 30 petals, plus 4 to 6 petaloids usually; arranged regularly.
*Form.*—From flat to high-centered; petals being more or less flat, but tending to be more erect at center of flower.
Petals:
*Texture.*—Leathery; thick.
*Appearance.* — Inside — velvety. Outside — from shiny to satiny.
*Shape.* — Outside — broadly obovate; sometimes crimped, wrinkled or fluted. Intermediate—broadly obovate, with apex being sometimes entire, but more often with one notch. Inside—obovate, with apex bluntly acute, usually flat, but sometimes faintly fluted.

This description of a newly opened flower was made from a rose grown outdoors during the month of June at Chino, California:

*Color.*—Outer petal: outside surface—base near white, with faint greenish tinge, and remainder being near Moderate Red, Plate 2.5R 4/10; inside surface—area about 5 mm. long at base near white, with slight greenish tinge, and remainder being between Moderate Red, Plate 2.5R 4/10 and Strong Red, Plate 5R 4/12, overlaid with Dark Red, Plate 2.5R 3/7 in varying degree, with one or two petals having an irregular narrow greenish-white vegetative streak from base to apex which occasionally fans out from base so that it is irregularly distributed over most of petal. Intermediate petal: outside surface—between Strong Purplish-Red, Plate 10RP 4/12 and Strong Purplish-Red, Plate 7.5RP 4/11, except for small greenish-white area at base; inside surface—between Moderate Red, Plate 2.5R 4/10 and Strong Red, Plate 5R 4/12, with varying degree of overlay of Dark Red, Plate 2.5R 3/7, except for small greenish-white spot at base. Inner petal: outside surface—often with greenish-white streak from base to apex, with remainder of petal being between Strong Purplish-Red, Plate 10RP 4/12 and Strong Purplish-Red, Plate 7.5R 4/11; inside surface—between Strong Purplish-Red, Plate 10RP 4/12 and Strong Red, Plate 5R 4/12, except for small greenish-white spot at base sometimes extending in the form of a streak half way to apex.

This description was made from a rose that was open for three days outdoors during the month of June at Chino:

*Color.*—Outer petal: outside surface—small spot at base of greenish-white, with remainder between Strong Purplish-Red, Plate 10RP 4/12 and Strong Purplish-Red, Plate 7.5RP 4/11; inside surface—small area at base of greenish-white, with remainder between Deep Purplish-Red, Plate 10RP 3/10 and Strong Purplish-Red, Plate 10RP 4/12, with slight hint of some shade of reddish-orange, and with one or two petals in outer row often having a ragged vegetative streak of greenish-white from base to apex, varying considerably in width so that occasionally this streak fans out over most of the petal. Inner petal: outside surface—base of greenish-white, with remainder between Strong Purplish-Red, Plate 7.5RP 5/12 and Moderate Purplish-Red, Plate 5RP 5/10; inside surface—base of greenish-white, with remainder between Strong Purplish-Red, Plate 10RP 4/12 and Strong Purplish-Red, Plate 7.5RP 4/11, occasionally with a greenish-white streak extending along midrib from base to apex.

*General color effect.*—Newly opened flower—near Strong Purplish-Red, Plate 10RP 4/12, with undertone varying from Strong Red, Plate 5R 4/12 to Vivid Red, Plate 5R 5/13. Three-days open—near Strong Purplish-Red, Plate 10RP 4/12, with undertone varying from Strong Red, Plate 5R 4/12 to Vivid Red, Plate 5R 5/13.

*Behavior.*—Drop off cleanly; not particularly affected by cold, hot, wet or dry weather.

*Flower longevity.*—On bush in garden—7 days in October. Cut roses grown outdoors and kept at living-room temperatures—9 days in October.

*Reproductive organs*

Stamens: Many; arranged regularly about pistils.
Filaments: From short to medium length; most with anthers. Color—white.
Anthers: Small; all open at once. Color—white, with yellow margins.
Pollen: Abundant. Color—gold.
Pistils: Medium quantity.
Styles; Uneven; from short to medium length; medium caliper; bunched.
Stigma: Color—greenish-white.
Ovaries: All enclosed in calyx.

Hips: Globular; occasionally with neck; smooth; relatively small for class; some hairs; walls thick and fleshy. Color—green and red while immature, becoming red and orange at maturity.
Sepals: Permanent; moderately long; fairly straight; somewhat variable in shape.
Seeds: From few to many; small.

*Plant*

Foliage:

*Leaves.*—Compound of 3–5 leaflets; moderately abundant; large size; heavy; leathery.

*Leaflets.*—Shape—ovoid, with apex from acute to acuminate. Base—from round to cuneate. Margin—both simply and doubly serrate.

*Color.*—Mature: upper surface—dark green; under surface—grey green. Young: upper surface—green, heavily overlaid with Deep Purplish-Red, Plate 10RP 3/10; under surface—grey green, with veins heavily stained with Deep Purplish-Red, Plate 10RP 3/10, overlaid on interveined areas to only a slightly lesser extent.

*Rachis (the supporting stem of the compound leaf).*—Medium weight. Upper side—grooved; ridges lined with stipitate glands. Under side—sparsely prickly; occasionally stipitate glands but otherwise smooth.

*Stipules.*—Short; narrow; with medium length points turning out at an angle of about 45°.

*Disease resistance.*—Better than average resistance to powdery mildew, as compared with other red floribunda roses grown under comparable field conditions at Chino, California.

Growth:

*Habit.*—Low; bushy; much-branched.

*Growth.*—Vigorous, but not tall.

*Canes.*—Medium caliper.

*Main stems.*—Color—dark green. Large prickles—few; medium length; straight; with short broad base; color—greyish-brown. Small prickles—few; color—grey brown. Hairs—none.

*Branches.*—Color—dark green. Large prickles—several; medium length; straight; with short, broad base; color—brown. Small prickles—few; color—brown. Hairs—none.

*New shoots.*—Color—green, overlaid with purplish-red. Large prickles—several; medium length; straight; with short broad base; color—purplish-red. Small prickles—few; color—purplish-red. Hairs—none.

We claim:

A new and distinct variety of rose plant of the floribunda class, substantially as herein shown and described, characterized particularly as to novelty by the unique combination of a relatively low-growing and compact habit of growth, flower buds of long-pointed to urn-shaped form, flowers ranging from small to medium size, with semi-double petalage, a habit of bearing the flowers in clusters composed of a relatively large number of flowers in each cluster, said flowers being borne in profusion, with consequent creation of an attractive mass effect which substantially covers the plant, a distinctive and attractive Bright Red general color tonality of the flowers, long-lasting flower qualities, and better than average resistance to powdery mildew.

No references cited.

ABRAHAM G. STONE, *Primary Examiner.*